United States Patent
Wan et al.

(10) Patent No.: US 11,318,105 B2
(45) Date of Patent: May 3, 2022

(54) METHOD FOR PREPARING ALBUMIN NANOPARTICLES BASED ON FREE RADICAL OXIDATION

(71) Applicant: HUAZHONG UNIVERSITY OF SCIENCE AND TECHNOLOGY, Hubei (CN)

(72) Inventors: Jiangling Wan, Hubei (CN); Han Luo, Hubei (CN); Jianyong Sheng, Hubei (CN); Xiangliang Yang, Hubei (CN)

(73) Assignee: HUAZHONG UNIVERSITY OF SCIENCE AND TECHNOLOGY, Hubei (CN)

( * ) Notice: Subject to any disclaimer, the term of this patent is extended or adjusted under 35 U.S.C. 154(b) by 0 days.

(21) Appl. No.: 17/292,455

(22) PCT Filed: Dec. 16, 2019

(86) PCT No.: PCT/CN2019/125591
§ 371 (c)(1),
(2) Date: May 10, 2021

(87) PCT Pub. No.: WO2020/135123
PCT Pub. Date: Jul. 2, 2020

(65) Prior Publication Data
US 2021/0322336 A1    Oct. 21, 2021

(30) Foreign Application Priority Data
Dec. 24, 2018  (CN) .......................... 201811581767.2

(51) Int. Cl.
| *A61K 9/51* | (2006.01) |
| *A61K 31/337* | (2006.01) |
| *A61K 47/42* | (2017.01) |
| *A61P 35/00* | (2006.01) |

(52) U.S. Cl.
CPC .......... *A61K 9/5192* (2013.01); *A61K 31/337* (2013.01); *A61K 47/42* (2013.01); *A61P 35/00* (2018.01)

(58) Field of Classification Search
CPC .......... A61K 9/00; A61K 9/51; A61K 31/337; A61K 47/42; A61P 35/00
See application file for complete search history.

(56) References Cited

U.S. PATENT DOCUMENTS

2014/0308351 A1* 10/2014 Perumal .................. A61K 9/14
424/489

FOREIGN PATENT DOCUMENTS

| CN | 1736489 | 2/2006 |
| CN | 102030898 | 4/2011 |
| CN | 104906589 | 9/2015 |
| CN | 108524452 | 9/2018 |
| WO | 2011019585 | 2/2011 |
| WO | 2016122414 | 8/2016 |

OTHER PUBLICATIONS

Caroline P. Baron et al., Oxidation of bovine serum albumin initiated by the Fenton reaction effect of EDTA, tert-butylhydroperoxide and tetra hydrofunran, Free Radical Research, 40(4), 409-417. (Year: 2006).*
Meysam Khosravifarsani et al., Effects of Fenton Reaction on Human Serum Albumin: An In Vivo Study, Electronin Physician, 8(9), 2970-2976. (Year: 2016).*
"International Search Report (Form PCT/ISA/210) of PCT/CN2019/125591", dated Mar. 20, 2020, with English translation thereof, pp. 1-4.

* cited by examiner

*Primary Examiner* — Michael G. Hartley
*Assistant Examiner* — Jagadishwar R Samala
(74) *Attorney, Agent, or Firm* — JCIP Global Inc.

(57) ABSTRACT

A method for preparing albumin nanoparticles based on free radical oxidation, comprising the following steps: preparing albumin aqueous solution with an albumin concentration of 1-20 mg/mL; (2) whilst stirring, adding free radical generating agent to the albumin aqueous solution, and continuing to stir and react for 1-60 min at 15-50° C.; the free radicals generated by the free radical generating agent are used for oxidizing the albumin, and the oxidized albumin molecules assemble to form albumin nanoparticles that are mainly bonded by hydrophobic action, thereby obtaining an albumin nanoparticle suspension. The present invention implements improvement by means of the key reaction mechanism of the nanoparticle preparation method and the corresponding design of the finishing process and, compared to the prior art, can effectively solve the problems of the complexity, high cost, and high toxicity of preparing nanoparticles.

5 Claims, 2 Drawing Sheets

METHOD FOR PREPARING ALBUMIN NANOPARTICLES BASED ON FREE RADICAL OXIDATION

CROSS-REFERENCE TO RELATED APPLICATION

This application is a 371 of international application of PCT application serial no. PCT/CN2019/125591, filed on Dec. 16, 2019, which claims the priority benefit of China application no. 201811581767.2, filed on Dec. 24, 2018. The entirety of each of the abovementioned patent applications is hereby incorporated by reference herein and made a part of this specification.

BACKGROUND

Field of the Disclosure

The invention belongs to the field of pharmaceutical preparations, and more specifically, relates to a method for preparing albumin nanoparticles based on free radical oxidation. The free radical oxidation method can be adopted to prepare soluble protein nanoparticles for injection. In particular, the invention can adopt hydroxyl radicals and sulfate radicals as initiators to change the hydrophilicity and hydrophobicity of the albumin molecule surface. The protein molecules are assembled mainly by means of hydrophobic interaction to form nanoparticles, which can encapsulate insoluble small molecule drugs.

Description of Related Art

Albumin accounts for the largest portion of protein in plasma, and serves as the transport carrier of many nutrients, such as ferrous ions, hormones, fatty acids and steroids. There are abundant sources of albumin, and albumin has good biocompatibility, biodegradability, low immunogenicity, and good solubility, can easily encapsulate hydrophobic drugs, has many functional groups, and is easy to modify. These advantages of albumin make albumin an ideal carrier in the pharmaceutical field. In 2005, the albumin-bound paclitaxel for injectable suspension (Abraxane®) developed by American Bioscience was approved by the US FDA for the treatment of metastatic breast cancer. This albumin injection has a particle size of about 130 nm, which not only can accumulate in tumor tissues through the EPR effect, but also specifically target tumor sites with high SPARC expression through receptor-mediated endocytosis. Clinical studies have shown that the paclitaxel protein nanoparticle has a higher therapeutic index and safety than its polyoxyethylene castor oil preparation (Taxol®), and avoids the use of corticosteroids for preoperative administration. It is shown that there are brightening prospects for serum albumin as carriers for intravenously injected drugs.

The conventional preparation method of albumin nanoparticles mainly involves chemical crosslinking and thermal denaturation. For example, in 2015, Li Fang et al. (CN104490847A) added vanillin analogs to form intramolecular disulfide bonds with free sulfhydryl groups in the albumin molecule under heating conditions, and the amino groups on the protein and the aldehyde groups of vanillin formed chemical bonds such as Schiff, thus obtaining stable nanoparticles in an aqueous solution. In 2013, Chen Daozhen et al. (CN103768024B) prepared ginsenoside Rh2 albumin composite nanoparticles by using anti-solvent and glutaraldehyde crosslinking methods. The thermal denaturation method is not suitable for drugs that are unstable to heat, and organic solvents are added more or less during the preparation process, such as chloroform, dichloromethane, etc. The addition of the organic solvents significantly increases the toxicity of the drug. Chemical crosslinking is non-specific, any nucleophilic groups (such as amines and hydroxyl groups) present in the protein structure are reactive, and the crosslinking agent such as glutaraldehyde that is used is toxic. American Bioscience has developed nab technology (Nanoparticle albumin-bound technology), which adopts albumin as a matrix and stabilizer to obtain albumin nanoparticles (U.S. Pat. No. 6,7530,06B1) without adding any emulsifiers and crosslinking agents. However, nab™ technology has the disadvantages of long cycle of preparation method and cumbersome process, high production cost, and there is an introduction of organic solvent chloroform, which is not easy to remove. CN102048695A discloses a method of albumin self-assembly, which uses mercaptoethanol as a reducing agent to open the disulfide bonds of albumin molecules, so that they can combine with each other to form nanoparticles by hydrophobic interaction. However, this method requires dialysis to remove excess reducing agent, which takes a long time and cannot realize industrial production. Currently, there is an urgent need for a drug-loaded albumin nanoparticle that can be fabricated through a simple process while the drug activity and toxicity are balanced based on the needs of human body.

SUMMARY OF THE DISCLOSURE

In view of the above defects or needs for improvement in the prior art, the purpose of the invention is to provide a method for preparing albumin nanoparticles based on free radical oxidation, in which improvement is achieved by means of the key reaction mechanism of the nanoparticle preparation method and the corresponding design of the finishing process and, compared to the prior art, can effectively solve the problems of the complexity, high cost, and high toxicity of preparing nanoparticles. The invention has simple processes and low production costs, and is suitable for large-scale industrial production. In this way, injectable albumin nanoparticle preparations can be obtained, especially drug-loaded albumin nanoparticle preparations.

In order to achieve the above purpose, according to an aspect of the invention, a method for preparing albumin nanoparticles based on free radical oxidation is provided, which is characterized in that the method includes the following steps:

(1) An albumin aqueous solution with an albumin concentration of 1-20 mg/mL is prepared.

(2) Whilst stirring, a free radical generating agent is added to the albumin aqueous solution obtained from the step (1), and the solution is stirred continuously and reacted for 1 to 60 minutes at 15 to 50° C. The free radicals generated by the free radical generating agent are used for oxidizing the albumin, and the oxidized albumin molecules assemble to form albumin nanoparticles that are mainly bonded by hydrophobic action. The reaction processes are all carried out through stirring.

As a preferable embodiment of the invention, in the step (2), the free radical is a hydroxyl radical or a sulfate radical; wherein the hydroxyl radical is generated from a Fenton reagent or a Fenton-like reagent, which undergoes a Fenton reaction or Fenton-like reaction. The sulfate radical is generated by activating and catalyzing persulfate decomposition. Preferably, the hydroxyl radical is generated through catalyzing hydrogen peroxide by ferrous ion, and the sulfate radical is generated through activating and catalyzing persulfate decomposition by ferrous ion.

As a preferred embodiment of the invention, in the step (2), the Fenton reagent is 8.8 mM of ferrous sulfate (FeSO4) solution, 88 mM of hydrogen peroxide solution and 0.1M of sodium citrate buffer with pH=4. The volume ratio of these three solutions satisfies 10:1:1, and the molar ratio between the hydrogen peroxide in the hydrogen peroxide solution and the albumin in the albumin aqueous solution is 2 to 5.

As a preferred embodiment of the invention, in the step (2), the persulfate is sodium persulfate, and the sulfate radical is generated by using ferrous ions to catalyze the decomposition of sodium persulfate, wherein the molar ratio between the ferrous ions and the sodium persulfate is 1:1, and the molar ratio between the sodium persulfate and the albumin in the albumin aqueous solution is 33 to 66.

As a preferred embodiment of the invention, in the step (1), the solute albumin used in the preparation of the albumin aqueous solution is at least one of human serum albumin, bovine serum albumin, recombinant human serum albumin, ovalbumin, goat serum albumin, murine serum albumin, donkey serum albumin, horse serum albumin, rabbit serum albumin, and porcine serum albumin, and is preferably at least one of human serum albumin, bovine serum albumin, and recombinant human serum albumin.

According to another aspect of the invention, the invention provides a method for preparing albumin nanoparticles for the delivery of hydrophobic anti-tumor drugs, and the method is characterized in including the following steps:

(1) An albumin aqueous solution with an albumin concentration of 1-20 mg/mL is prepared.

(2) Whilst stirring, a free radical generating agent is added to the albumin aqueous solution obtained from the step (1). After the solution is reacted for 1 to 10 minutes at 15 to 50° C., an ethanol solution of hydrophobic anti-tumor drug is added thereto and reacted continuously for 1 to 10 minutes. The free radicals generated by the free radical generating agent are used for oxidizing the albumin, and the oxidized albumin molecules assemble to form albumin nanoparticles that are mainly bonded by hydrophobic action, and the hydrophobic anti-tumor drug is encapsulated in these albumin nanoparticles, thereby obtaining the albumin nanoparticle suspension encapsulating the hydrophobic anti-tumor drug, and these reaction processes are all carried out through stirring. The hydrophobic anti-tumor drug promotes the formation of albumin nanoparticles because of its hydrophobicity, and enhances the uniformity and stability of the generated albumin nanoparticles.

As a preferred embodiment of the invention, in the step (2), the hydrophobic anti-tumor drug is one or a mixture of two or more of paclitaxel, docetaxel, cabazitaxel, and 10-hydroxycamptothecin; preferably the drug is paclitaxel.

Through the above technical solutions conceived by the invention, compared with the prior art, since free radicals are used as initiators, the hydrophilicity and hydrophobicity of protein molecules are changed, and the protein molecules are assembled through hydrophobic interaction to form nanoparticles, which can encapsulate insoluble small-molecule drugs. The preparation method of albumin nanoparticles in the invention is particularly applicable to the preparation of carriers for anti-tumor drugs. Specifically, the invention has the following technical effects.

1. Compared with the conventional preparation method of albumin nanoparticles, the method in the invention introduces no toxic reagents and has higher biological safety.

2. Compared with Nab™ technology, in the method of the invention, the process flow is simple, the encapsulation rate is high, the loss during preparation is less, the process is easy for industrialization, the ingredients are simple, and no toxic reagents are introduced.

3. The invention can take advantage of the high permeability and retention effect of nanoparticles on tumors as well as the targeting effect of albumin molecules themselves, such that more drugs can be accumulated in tumor tissues, thereby improving anti-tumor effects, and reducing toxic side effects. The invention retains the advantages of albumin as a carrier, utilizes the EPR effect of albumin carrier and the ability to actively target tumors, improves the accumulation of drugs in tumor sites, and has a higher therapeutic index and safety as compared with conventional Taxol preparations.

In the prior art, Abraxane® is prepared by nanoparticle albumin-bound technology (nab™). In the technology, preliminary emulsion is prepared through high-shear preparation, high-pressure homogenization is performed to obtain refined emulsion, and then rotary evaporation is carried out to remove the organic solvent chloroform. The whole preparation process is cumbersome and requires the use of toxic solvent chloroform. Here, the invention provides a method for preparing albumin nanoparticles based on free radical oxidation. Most of the amino acid residues in albumin that are sensitive to free radical oxidation are located in the hydrophobic pocket of albumin. After these amino acid residues are oxidized, their polarity increases, resulting in the exposure of the hydrophobic domain and changes in protein conformation. The oxidation of free radicals causes the hydrophobic pockets of albumin to be exposed and the hydrophobicity of the protein surface increases. When the hydrophobicity of the protein surface increases to a certain extent, the protein molecules gather together through hydrophobic and electrostatic interactions to form uniform nanoparticles. Due to the rapid and dramatic reaction of free radicals and various reaction ways, we have optimized the generating method and dosage of free radical initiators, and optimized the reaction conditions that are simple, easy to control, environmentally friendly, and low-cost. The Fenton reaction is one of the typical methods of generating hydroxyl radicals. Specifically, hydrogen peroxide produces highly reactive hydroxyl radicals .OH under the catalysis of ferrous ions, .OH can quickly generate a chain reaction with most organic pollutants, and non-selectively oxidize harmful substances into $CO_2$, $H_2O$ or mineral salts, without causing secondary pollution, and is now mainly used for processing organic waste water. The invention uses hydroxyl radicals generated by Fenton's reagent to initiate albumin self-assembly, that is, albumin molecules oxidized by free radicals aggregate to form nanoparticles through hydrophobic interaction, and blank and drug-loaded albumin nanoparticles can be obtained. The oxidation-reduction potential of sulfate radicals is similar to that of OH., which can be produced by catalyzing activated persulfate by transition metal at room temperature, and the process is highly efficient, non-toxic, and low in price. Moreover, the invention also utilizes sulfate radicals generated by persulfate activation to initiate albumin self-assembly, thereby obtaining uniform albumin nanoparticles.

BRIEF DESCRIPTION OF THE DRAWINGS

In FIG. 1, a) is the DLS particle size distribution of blank albumin nanoparticles in Example 1, and b) is the DLS particle size distribution of the albumin nanoparticles loaded with paclitaxel. It is shown that the distribution of drug-loaded albumin nanoparticles is narrower than that of blank albumin nanoparticles. The reason might be that the hydrophobic paclitaxel provides a hydrophobic core for the assembly of albumin, which facilitates the formation of albumin nanoparticles loaded with paclitaxel.

In FIG. 2, a) is the TEM image of the blank albumin nanoparticles in Example 1, and b) is the TEM image of the albumin nanoparticles loaded with paclitaxel in Example 7. Corresponding to the DLS diagram in FIG. 1, the shape of the drug-loaded albumin nanoparticles is more rounded and the size distribution is more uniform.

DESCRIPTION OF EMBODIMENTS

Figure 1:
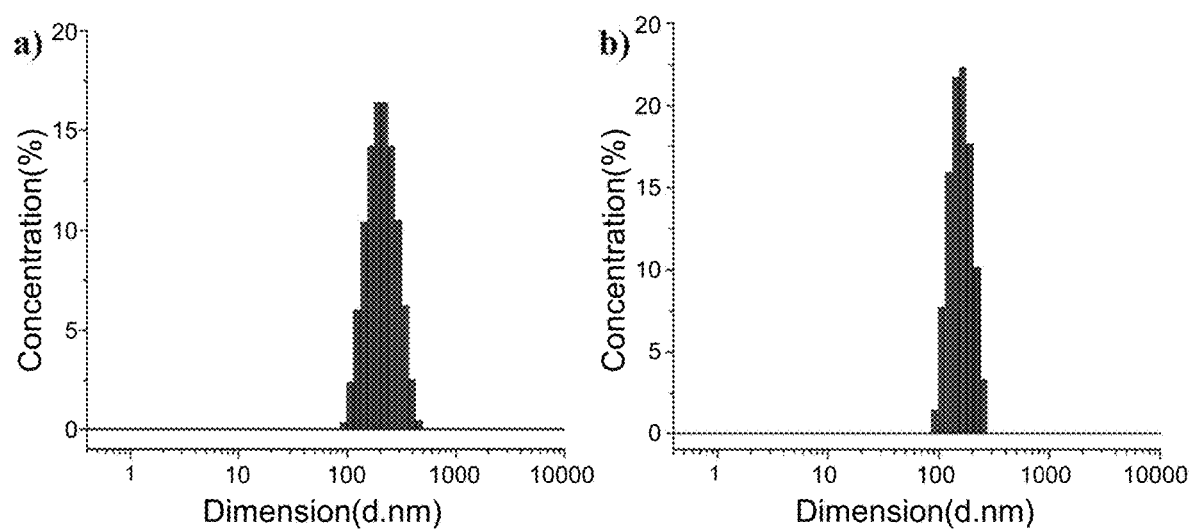
FIG. 1 shows the particle size distribution diagrams of blank albumin nanoparticles and drug-loaded albumin nanoparticles.
Figure 2:
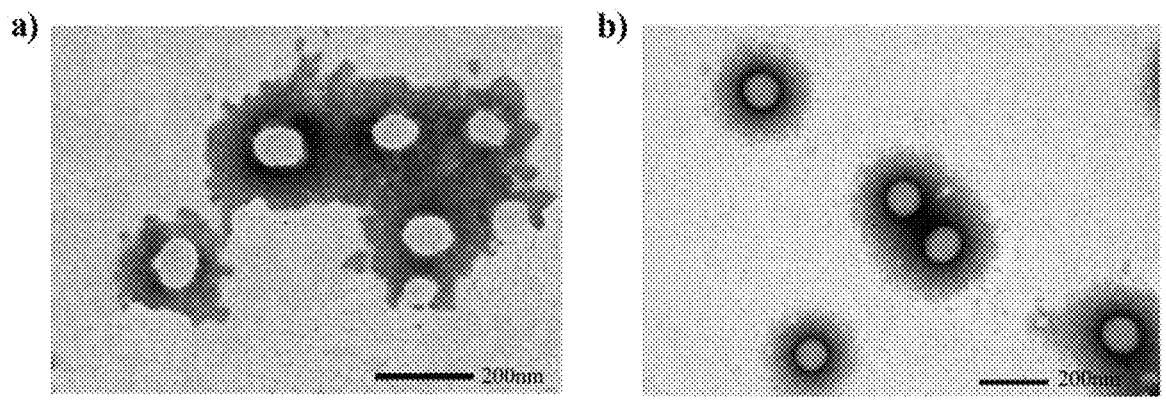
FIG. 2 shows the electron micrographs of blank albumin nanoparticles and drug-loaded albumin nanoparticles.
Figure 3:
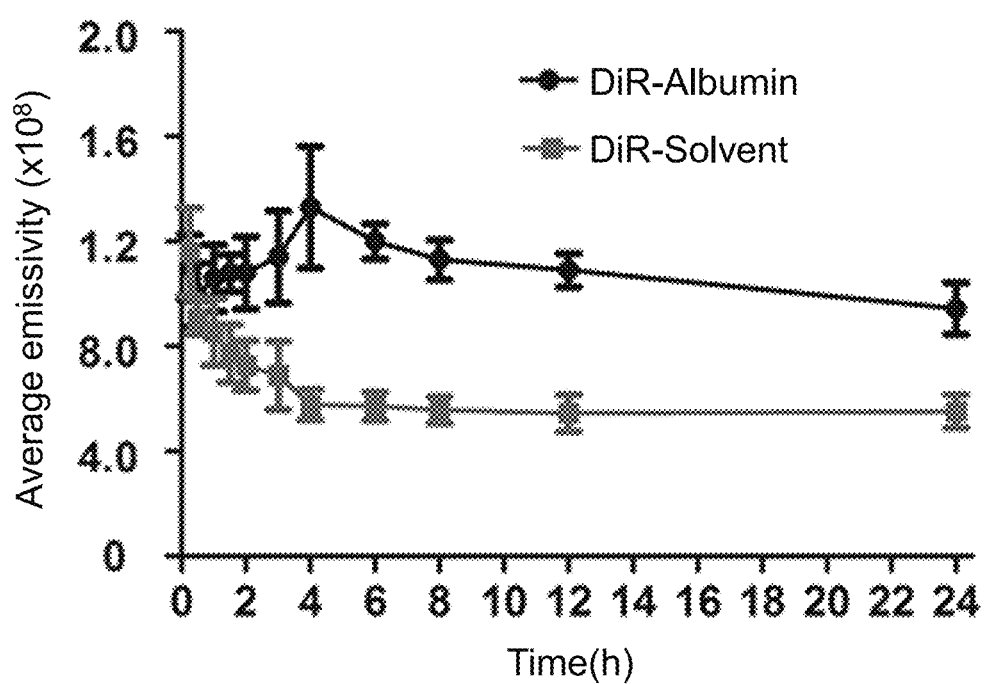
FIG. 3 shows the accumulation of DiR at the tumor site changes over time after intravenous injection of the DiR-loaded nanoparticles or the DiR solution (the solvent is polyoxyethylene castor oil and absolute ethanol, the volume ratio is 1:1) to tumor-bearing mice. The results showed that the accumulation of DiR in the tumor site of the albumin group is significantly higher than that of the DiR solution, indicating that albumin encapsulation is beneficial to improve the targeting of drugs in tumor tissues, thereby improving the anti-tumor effect.

In order to make the objectives, technical solutions and advantages of the present disclosure clearer, the following further describes the present disclosure in detail with reference to the accompanying drawings and embodiments. It should be understood that the specific embodiments described here are only used to explain the present disclosure, but not to limit the present disclosure. In addition, the technical features involved in the various embodiments of the present invention described below can be combined with each other as long as they do not conflict with each other.

EXAMPLE 1

Preparation of Bovine Serum Albumin Nanoparticles using Hydroxyl Radicals Produced by Fenton Reaction as Initiator 200 mg of bovine serum albumin (98%, 68KD, Roche) is dissolved in 10 mL of deionized water, and 1000 μL of Fenton's reagent (8.8 mM of ferrous sulfate ($FeSO_4$) solution, 88 mM of hydrogen oxide solution and 0.1M of sodium citrate buffer solution with pH=4, the volume ratio of the three solutions is 10:1:1) is added under a water bath at 37° C. After reacting for 2 to 10 minutes, the albumin nanoparticle suspension is obtained. The above reaction processes are all carried out through stirring. The average particle size of albumin nanoparticles is 130 to 180 nm, and the Zeta potential is about −15 mV (Malvern, Zetasizer Nano ZSP).

EXAMPLE 2

Preparation of Bovine Serum Albumin Nanoparticles using Hydroxyl Radicals Produced by Fenton Reaction as Initiator 100 mg of bovine serum albumin (98%, 68KD, Roche) is dissolved in 10 mL of deionized water, and 500 μL of Fenton's reagent (8.8 mM of ferrous sulfate ($FeSO_4$) solution, 88 mM of hydrogen oxide solution and 0.1M of sodium citrate buffer solution with pH=4, the volume ratio of the three solutions is 10:1:1) is added under a water bath at 15° C. After reacting for 10 to 60 minutes, the albumin nanoparticle suspension is obtained. The above reaction processes are all carried out through stirring. The average particle size of albumin nanoparticles is 180 to 275 nm, and the Zeta potential is about −15 mV (Malvern, Zetasizer Nano ZSP).

EXAMPLE 3

Preparation of Bovine Serum Albumin Nanoparticles using Hydroxyl Radicals Produced by Fenton Reaction as Initiator 10 mg of bovine serum albumin (98%, 68KD, Roche) is dissolved in 10 mL of deionized water, and 50 μL of Fenton's reagent (8.8 mM of ferrous sulfate ($FeSO_4$) solution, 88 mM of hydrogen oxide solution and 0.1M of sodium citrate buffer solution with pH=4, the volume ratio of the three solutions is 10:1:1) is added under a water bath at 50° C. After reacting for 1 to 10 minutes, the albumin nanoparticle suspension is obtained. The above reaction processes are all carried out through stirring. The average particle size of albumin nanoparticles is 130 to 200 nm, and the Zeta potential is about −15 mV (Malvern, Zetasizer Nano ZSP).

EXAMPLE 4

Preparation of Bovine Serum Albumin Nanoparticles using Sulfate Radicals Produced by the Decomposition of Sodium Persulfate Catalyzed by Ferrous Ions as Initiators 10 mg of bovine serum albumin (98%, 68KD, Roche) is dissolved in 10 mL of deionized water, and 10 μL of sulfate radical is added as initiator (1M of $FeSO_4$, 1M of sodium persulfate PS, the volume ratio of the two solutions is 1:1) under a water bath at 25° C. After reacting for 1 to 10 minutes, the albumin nanoparticle suspension is obtained. The above reaction processes are all carried out through stirring. The average particle size of albumin nanoparticles is 80 to 95 nm (Malvern, Zetasizer Nano ZSP).

EXAMPLE 5

Preparation of Bovine Serum Albumin Nanoparticles using Sulfate Radicals Produced by the Decomposition of Sodium Persulfate Catalyzed by Ferrous Ions as Initiators 10 mg of bovine serum albumin (98%, 68KD, Roche) is dissolved in 10 mL of deionized water, and 20 μL of sulfate radical is added as initiator (1M of $FeSO_4$, 1M of sodium persulfate PS, the volume ratio of the two solutions is 1:1) under a water bath at 25° C. After reacting for 10 minutes, the albumin nanoparticle suspension is obtained. The above reaction processes are all carried out through stirring. The average particle size of albumin nanoparticles is about 160 nm (Malvern, Zetasizer Nano ZSP).

EXAMPLE 6

Preparation of Bovine Serum Albumin Nanoparticles Loaded with Paclitaxel using Hydroxyl Radicals Produced by Fenton Reaction as Initiator 10 mg of bovine serum albumin (98%, 68 KD, Roche) is dissolved in 10 mL of deionized water, and 50 μL of Fenton's reagent (8.8 mM of ferrous sulfate (FeSO$_4$) solution, 88 mM of hydrogen oxide solution and 0.1M of sodium citrate buffer solution with pH=4, the volume ratio of the three solutions is 10:1:1) is added under a water bath at 25° C. After reacting for 2 minutes, 75 μL of 40 mg/mL paclitaxel ethanol solution is added, and the reaction is continued for 10 minutes to obtain the albumin nanoparticle loaded with paclitaxel. The above reaction processes are all carried out through stirring. The average particle size of albumin nanoparticles is 150 nm (Malvern, Zetasizer Nano ZSP). HPLC analysis shows that the paclitaxel drug loading in this experiment reached 18.8%.

EXAMPLE 7

Preparation of Bovine Serum Albumin Nanoparticles Loaded with Docetaxel Using Hydroxyl Radicals Produced by Fenton Reaction as Initiator 100 mg of bovine serum albumin (98%, 68KD, Roche) is dissolved in 10 mL of deionized water, and 500 μL of Fenton's reagent (8.8 mM of ferrous sulfate (FeSO$_4$) solution, 88 mM of hydrogen oxide solution and 0.1M of sodium citrate buffer solution with pH=4, the volume ratio of the three solutions is 10:1:1) is added under a water bath at 25° C. After reacting for 2 minutes, 250 μL of 40 mg/mL docetaxel ethanol solution is added, and the reaction is continued for 10 minutes to obtain the albumin nanoparticle suspension loaded with docetaxel. The above reaction processes are all carried out through stirring. The average particle size of albumin nanoparticles is 160 nm (Malvern, Zetasizer Nano ZSP). HPLC analysis shows that the docetaxel encapsulation rate in this experiment reached 97%.

EXAMPLE 8

Preparation of Bovine Serum Albumin Nanoparticles Loaded with Fluorescent Dye DiR using Hydroxyl Radicals Produced by Fenton Reaction as Initiator 100 mg of bovine serum albumin (98%, 68 KD, Roche) is dissolved in 10 mL of deionized water, and 500 μL of Fenton's reagent (8.8 mM of ferrous sulfate (FeSO$_4$) solution, 88 mM of hydrogen oxide solution and 0.1M of sodium citrate buffer solution with pH=4, the volume ratio of the three solutions is 10:1:1) is added under a water bath at 25° C. After reacting for 2 minutes, 25 μL of DiR mother liquor (5 mg/mL, DMSO and absolute ethanol as solvents, their volume ratio is 1:4) is added, and the reaction is continued for 10 minutes to obtain the albumin nanoparticle loaded with DiR. The above reaction processes are all carried out through stirring. The average particle size of albumin nanoparticles loaded with DiR is 140 nm (Malvern, Zetasizer Nano ZSP).

EXAMPLE 9

Evaluation of Tumor Targeting Ability of Albumin Nanoparticles Loaded with Fluorescent Dye DiR after Intravenous Injection into 4T1 Tumor-Bearing Mice DiR-loaded albumin nanoparticles are prepared according to Example 8. In the meantime, the DiR mother liquor is diluted with Taxol solvent (polyoxyethylene castor oil and absolute ethanol, their volume ratio is 1:1) to the same concentration, and the two DiR preparations are intravenously injected to the tumor-bearing Balb/c mice inoculated with 4T1. Thereafter, the tumor targeting effect is assessed.

The mouse breast cancer 4T1 cells in the logarithmic growth phase with good condition are obtained. The cells are digested with 0.25% trypsin to make them become single cells. After washing them twice with PBS, the cell concentration is adjusted to $1 \times 10^7$ cell/ml by using normal saline through a cell counting method. Each healthy Balb/c female mouse is inoculated subcutaneously with 0.1 ml (containing $1 \times 10^6$ live cells) on their right back and waist. During the feeding process, the mice in each group are equally free to eat and drink, and kept in the animal room under the humidity of 20 to 30%. When the subcutaneous tumor volume reached 200 mm$^3$ (about 2 weeks), the tumor-bearing mice are randomly divided into 2 groups, and 100 μL of two DiR preparations are injected into their tail vein respectively. In vivo imaging of mice (IVIS Lumina XR, Caliper, US) is performed within 0.25, 0.5, 1, 2, 3, 4, 6, 8, and 12 hours after administration. It can be seen that the amount of accumulation of DiR at the tumor site is significantly increased in the albumin group.

In addition to the specific types of albumin used in the above examples, the invention can also use other types of albumin as required. For example, human serum albumin, bovine serum albumin, recombinant human serum albumin, ovalbumin, goat serum albumin, murine serum albumin, donkey serum albumin, horse serum albumin, rabbit serum albumin, and porcine serum albumin are all applicable. Particularly, human serum albumin, bovine serum albumin, recombinant human serum albumin or a combination of the above can be adopted.

Those skilled in the art can easily understand that the above descriptions are only preferred embodiments of the present invention and are not intended to limit the present invention. Any modification, equivalent replacement and improvement, and the like made based on the spirit and principle of the present invention should fall within the scope of the present invention.

What is claimed is:

1. A method for preparing albumin nanoparticles based on free radical oxidation, characterized in comprising the following steps:
    (1) preparing an albumin aqueous solution with an albumin concentration of 1-20 mg/mL;
    (2) whilst stirring, adding a free radical generating agent to the albumin aqueous solution obtained from the step (1), and reacting the solution for 1 to 60 minutes at 15 to 50° C., using a free radical generated by the free radical generating agent for oxidizing the albumin, wherein the oxidized albumin molecules assemble to form the albumin nanoparticles that are mainly bonded by a hydrophobic action, and the reaction processes are all carried out through stirring,
    wherein, in the step (2), the free radical is a hydroxyl radical or a sulfate radical, the hydroxyl radical is generated from a Fenton reagent, which undergoes a Fenton reaction, the sulfate radical is generated by activating and catalyzing persulfate decomposition, and wherein the hydroxyl radical is generated through catalyzing hydrogen peroxide by ferrous ions, and the sulfate radical is generated through activating and catalyzing persulfate decomposition by ferrous ions, and
    the Fenton reagent is a 8.8 mM of ferrous sulfate (FeSO4) solution, a 88 mM of hydrogen peroxide solution and a 0.1M of sodium citrate buffer with pH=4, and a volume ratio of these three solutions satisfies 10:1:1, and a molar ratio between the hydrogen peroxide in the hydrogen peroxide solution and the albumin in the albumin aqueous solution is 2 to 5.

2. The method for preparing the albumin nanoparticles based on free radical oxidation according to claim 1, characterized in that, in the step (2), the persulfate is sodium persulfate, and the sulfate radical is generated by using the ferrous ions to catalyze the decomposition of the sodium persulfate, wherein a molar ratio between the ferrous ions and the sodium persulfate is 1:1, and a molar ratio between the sodium persulfate and the albumin the albumin aqueous solution is 33 to 66.

3. The method for preparing the albumin nanoparticles based on free radical oxidation according to claim 1, characterized in that, in the step (1), the solute albumin used in the preparation of the albumin aqueous solution is at least one of human serum albumin, bovine serum albumin, recombinant human serum albumin, ovalbumin, goat serum albumin, murine serum albumin, donkey serum albumin, horse serum albumin, rabbit serum albumin, and porcine serum albumin.

4. A method for preparing albumin nanoparticles for delivery of hydrophobic anti-tumor drugs, characterized in that the method comprises the following steps:
   (1) preparing an albumin aqueous solution with an albumin concentration of 1-20 mg/mL;
   (2) whilst stirring, adding a free radical generating agent to the albumin aqueous solution obtained from the step (1), and reacting the solution for 1 to 10 minutes at 15 to 50° C., then adding an ethanol solution of a hydrophobic anti-tumor drug thereto and reacting the solution continuously for 1 to 10 minutes, and using a free radical generated by the free radical generating agent for oxidizing the albumin, wherein the oxidized albumin molecules assemble to form the albumin nanoparticles that are mainly bonded by a hydrophobic action, and the hydrophobic anti-tumor drug is encapsulated in the albumin nanoparticles, thereby obtaining the albumin nanoparticle encapsulating the hydrophobic anti-tumor drug, and the reaction processes are all carried out through stirring, wherein the hydrophobic anti-tumor drug promotes the formation of the albumin nanoparticles because of its hydrophobicity, and enhances the uniformity and stability of the generated albumin nanoparticles, wherein, in the step (2), the free radical is a hydroxyl radical or a sulfate radical, the hydroxyl radical is generated from a Fenton reagent, which undergoes a Fenton reaction, the sulfate radical is generated by activating and catalyzing persulfate decomposition, and wherein the hydroxyl radical is generated through catalyzing hydrogen peroxide by ferrous ions, and the sulfate radical is generated through activating and catalyzing persulfate decomposition by ferrous ions, and the Fenton reagent is a 8.8 mM of ferrous sulfate (FeSO4) solution, a 88 mM of hydrogen peroxide solution and a 0.1M of sodium citrate buffer with pH=4, and a volume ratio of these three solutions satisfies 10:1:1, and a molar ratio between the hydrogen peroxide in the hydrogen peroxide solution and the albumin in the albumin aqueous solution is 2 to 5.

5. The method for preparing the albumin nanoparticles for delivery of the hydrophobic anti-tumor drugs according to claim 4, characterized in that, in the step (2), the hydrophobic anti-tumor drug is one or a mixture of two or more of paclitaxel, docetaxel, cabazitaxel, and 10-hydroxycamptothecin.

* * * * *